US010695383B2

(12) United States Patent
Ooishi et al.

(10) Patent No.: US 10,695,383 B2
(45) Date of Patent: Jun. 30, 2020

(54) CIRCADIAN RHYTHM-IMPROVING AGENT

(71) Applicants: National Institute of Advanced Industrial Science and Technology, Chiyoda-ku (JP); Sapporo Holdings Limited, Shibuya-ku (JP)

(72) Inventors: Katsutaka Ooishi, Tsukuba (JP); Koyomi Miyazaki, Tsukuba (JP); Nanako Itoh, Tsukuba (JP); Saori Yamamoto, Tsukuba (JP); Yasukazu Nakakita, Shibuya-ku (JP); Hirotaka Kaneda, Shibuya-ku (JP)

(73) Assignees: National Institute of Advanced Industrial Science and Technology, Tokyo (JP); Sapporo Holdings Limited, Tokyo (JP)

( * ) Notice: Subject to any disclaimer, the term of this patent is extended or adjusted under 35 U.S.C. 154(b) by 262 days.

(21) Appl. No.: 14/382,193

(22) PCT Filed: Feb. 8, 2013

(86) PCT No.: PCT/JP2013/053091
§ 371 (c)(1),
(2) Date: Aug. 29, 2014

(87) PCT Pub. No.: WO2013/129085
PCT Pub. Date: Sep. 6, 2013

(65) Prior Publication Data
US 2015/0064151 A1  Mar. 5, 2015

(30) Foreign Application Priority Data
Mar. 2, 2012  (JP) ................ 2012-046806

(51) Int. Cl.
  *A61K 35/74*  (2015.01)
  *A23L 2/38*  (2006.01)
  *A23L 33/135*  (2016.01)
  *A61K 35/744*  (2015.01)
  *A23L 2/52*  (2006.01)

(52) U.S. Cl.
  CPC .............. *A61K 35/74* (2013.01); *A23L 2/382* (2013.01); *A23L 2/52* (2013.01); *A23L 33/135* (2016.08); *A61K 35/744* (2013.01); *A23V 2002/00* (2013.01); *A23Y 2220/13* (2013.01)

(58) Field of Classification Search
  None
  See application file for complete search history.

(56) References Cited

U.S. PATENT DOCUMENTS

| 2007/0207134 | A1 | 9/2007 | Moriyama et al. | |
| 2008/0176305 | A1* | 7/2008 | Sato | A23C 11/106 435/170 |
| 2010/0150891 | A1 | 6/2010 | Beppu et al. | |
| 2011/0002901 | A1* | 1/2011 | Segawa | A23L 1/3014 424/93.45 |
| 2012/0009163 | A1* | 1/2012 | Sawada | A61K 35/744 424/93.44 |

FOREIGN PATENT DOCUMENTS

| EP | 1 741 437 A1 | 1/2007 |
| EP | 2 062 968 A1 | 5/2009 |
| EP | 2 251 019 A1 | 11/2010 |
| JP | 2008-179573 | 8/2008 |
| JP | 2012-17282 | 1/2012 |
| JP | 2012-36158 | 2/2012 |
| WO | WO 2005/094849 A1 | 10/2005 |
| WO | WO 2008/120713 A1 | 10/2008 |

OTHER PUBLICATIONS

Liu et al., GABA Synchronizes Clock Cells within the Suprachiasmatic Circadian Clock, 2000, vol. 25, pp. 123-128.*
Ueno et al., "Heat-killed body of Lactobacillus brevis SBC8803 Ameliorates Intestinal Injury in a Murine Model of Colitis by Enhancing the Intestinal Barrier Function", Inflamm. Bowel Dis., vol. 17, No. 11, 2011, pp. 2235-2250.*
Kumar et al., "Abnormal REM sleep in the Irritable Bowel Syndrome", Gastroenterology, 1992, vol. 103, pp. 12-17.*
Horrii et al., "Effects of intraduodenal injection of Lactobacillus brevis SBC8803 on autonomic neurotransmission and appetite in rodents", Neurosci. Letters, Feb. 28, 2013;539:32-7. doi: 10.1016/j.neulet.2013.01.037. Epub Feb. 4, 2013.*
Green et al., Aliment Pharmacol Ther 1998; 12: pp. 1207-1216.*
Basta et al., Chronic Insomnia and Stress System, Sleep Med Clin. Jun. 2007; vol. 2, issue 2: pp. 279-291.*
Dodson et al., Therpeutics for Circadian Rhythm Sleep Disorders, Sleep Med Clin. Dec. 2010; vol. 5, issue 4: pp. 701-715.*
Horii et al., Current Topics in Nutraceutical Research, vol. 13, No. 1, pp. 47-54 (2015).*
International Preliminary Report on Patentability and Written Opinion dated Sep. 12, 2014, in International application No. PCT/JP2013/053091.
International Search Report dated Mar. 5, 2013, in International application No. PCT/JP2013/053091.
Shinji Itoh, et al., "Diminished Circadian Rhythm of Locomotor Activity after Vagotomy in Rats", *Japanese Journal of Physiology*, vol. 31,No. 6, 1981, pp. 957-961.
Hideki Bando, et al., "Circadian Rhythms in the Larynx and Trachea under the Control of the Molecular Clock", The Larynx Japan, vol. 22, 2010, pp. 77-82, with English Abstract.
Charlotte Von Gall, et al., "Melatonin Plays a Crucial Role in the Regulation of Rhythmic Clock Gene Expression in the Mouse Pars Tuberalis", Ann. N.Y. Acad. Sci., 2005, vol. 1040, pp. 508-511.

(Continued)

*Primary Examiner* — Scott Long
*Assistant Examiner* — Evelyn Y Pyla
(74) *Attorney, Agent, or Firm* — Morgan, Lewis & Bockius LLP

(57) ABSTRACT

The invention provides an agent for improving circadian rhythm comprising cells of lactic acid bacterium or treated product thereof as an active ingredient.

13 Claims, 6 Drawing Sheets

(56) References Cited

OTHER PUBLICATIONS

Extended European Search Report dated Jan. 4, 2016 in Patent Application No. 13754034.0.
Office Action dated Apr. 6, 2018 in corresponding European Patent Application No. 13 754 034.0, 6 pages.
S. Yamamura et al, "The effect of *Lactobacillus helveticus* Fermented Milk on Sleep and Health Perception in Elderly Subjects", European Journal of Clinical Nutrition, Nature Publishing Group, GB, vol. 63, No. 1, XP008120343, Jan. 1, 2009, pp. 100-105.

* cited by examiner

Fig. 6
(A)
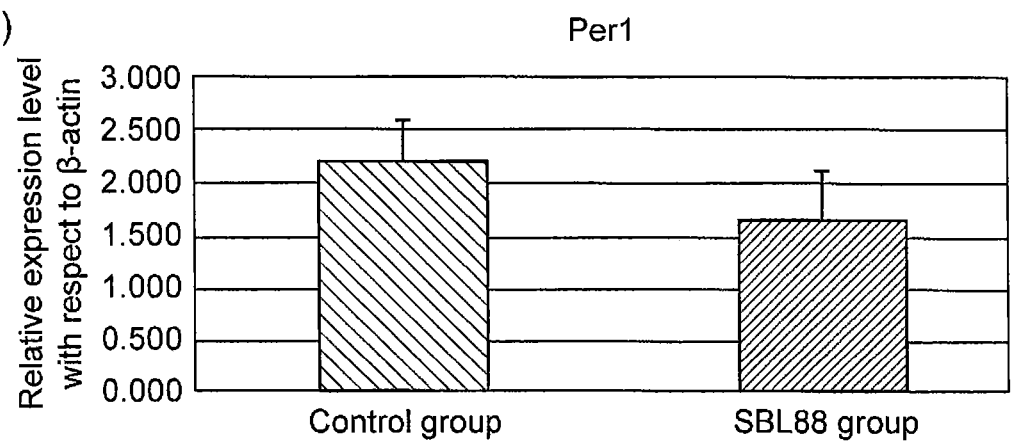
(B)
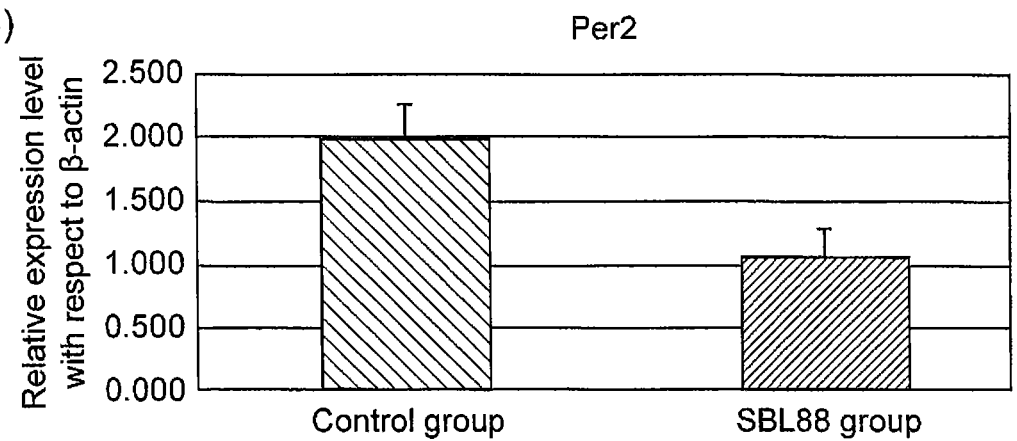
(C)
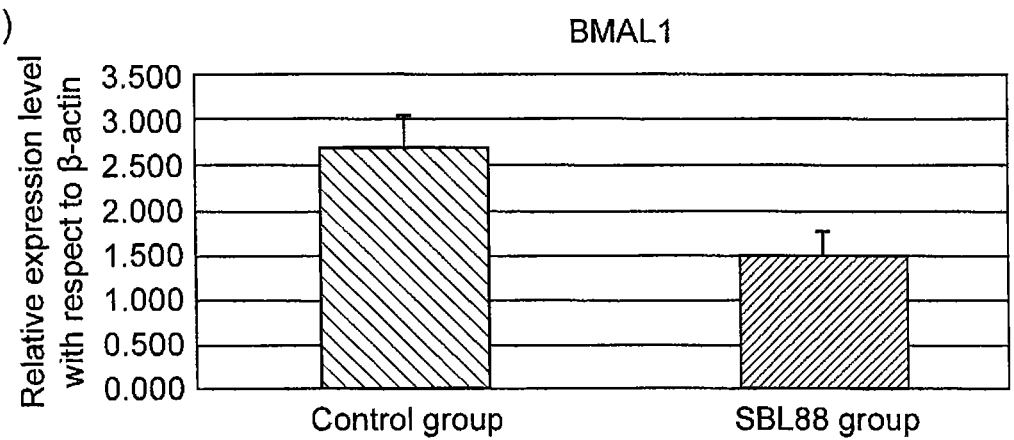

CIRCADIAN RHYTHM-IMPROVING AGENT

TECHNICAL FIELD

The present invention relates to an agent for improving circadian rhythm.

BACKGROUND ART

The circadian rhythm is a physiological phenomenon that fluctuates with a period of approximately 24 hours. The circadian rhythm is found in biological activity including brain waves, hormone secretion, and cellular regeneration, and it plays an important role in determining sleeping and eating patterns. Disturbance of circadian rhythm or reduction in circadian rhythm function causes various alterations such as sleep disorder, insomnia, autonomic imbalance and endocrine dysfunction.

It is in light of this that agents for improving circadian rhythm capable of restoring circadian rhythm disturbance or circadian rhythm function are thought to be useful. Patent literature 1, for example, discloses a functional composition that modulates circadian rhythm, comprising a lactic acid bacteria fermentate of soybean milk as an active ingredient. Also, patent literature 2 discloses an agent for improving circadian rhythm comprising whey as an active ingredient.

CITATION LIST

Patent Literature

[Patent literature 1] JP 2008-179573 [Patent literature 2] WO2005/094849

SUMMARY OF INVENTION

Technical Problem

In modern society, it is said that disturbance of the circadian rhythm or reduction in circadian rhythm function due to day/night irregularity or irregular dietary habits, is responsible for sleep disorders of different types, which are found in 1 out of every five Japanese (particularly 1 out of three for those over age 60). Sleep disorder is a risk factor for psychiatric conditions such as depression and school absenteeism, as well as hypertension, heart disease and cerebrovascular disease, while it also causes traffic accidents, and thus sleep disorder results in various social problems. According to published sources, the economic loss attributed to sleep disorder in Japan in 2006 was 3.5 trillion yen for the year.

Antidepressant drugs and tranquilizers that are used to improve sleep disorder are associated with the risk of producing dependency with prolonged administration, and side-effects. There is therefore much anticipation for development of drugs and foods that exhibit milder action and reduce such risks. In addition, it would be more effective if sleep disorder could be improved by improving circadian rhythm.

Several agents for improving circadian rhythm are already known (Patent literature 1 and 2, for example). However, it still cannot be said that sufficient options exist for satisfying the myriad needs of consumers. It is therefore an object of the present invention to provide a novel agent for improving circadian rhythm.

Solution to Problem

The present inventors have found that an effect of improving circadian rhythm is exhibited by the strain of lactic acid bacterium *Lactobacillus brevis* SBC8803 itself, or treated products thereof. The present invention is based on this newly acquired knowledge.

Specifically, the invention provides an agent for improving circadian rhythm comprising cells of lactic acid bacterium or treated product thereof as an active ingredient.

Lactic acid bacteria have long been utilized as fermented foods, and their safety in the body has been established. Therefore, this agent for improving circadian rhythm does not carry the risk of dependency or side-effects. Furthermore, although reports already exist of improving circadian rhythm by lactic acid fermentates (soybean milk lactic acid fermentate, whey and the like), improvement of circadian rhythm by the cells of lactic acid bacteria or their treated products themselves is not known. Lactic acid fermentates can only be added to a limited range of foods and beverages because of their own flavor, but since the cells of lactic acid bacteria and their treated products themselves do not produce any particular flavor, they can be added to a wide range of foods and beverages. The agent for improving circadian rhythm described above is advantageous from this viewpoint as well.

The lactic acid bacteria are preferably lactic acid bacteria belonging to *Lactobacillus brevis*, and more preferably they are of *Lactobacillus brevis* SBC8803. This allows an even more excellent circadian rhythm-improving effect to be obtained.

*Lactobacillus brevis* has long been known as a lactic acid bacterium used in fermented foods, and its safety in the body has been adequately established. Because of its high safety in the body, it can be continuously ingested for prolonged periods.

*Lactobacillus brevis* SBC8803 is a strain that has been deposited at the International Patent Organism Depositary (IPOD) of the National Institute of Advanced Industrial Science and Technology (Central 6, 1-1, Higashi 1-chome, Tsukuba City, Ibaraki Prefecture, Japan 305-8566) on Jun. 28, 2006, as FERM BP-10632. Throughout the present specification, this strain will be also referred to as "strain SBL88".

The agent for improving circadian rhythm can normalize the mRNA expression level of clock genes. Thus, the circadian rhythm-improving effect of the agent for improving circadian rhythm described above can be obtained based at least partially on normalization of mRNA expression levels of clock genes. Such clock genes may be, for example, Per2 or Bma11.

Since the agent for improving circadian rhythm can improve the sleep-wake rhythm by improving circadian rhythm, it may also be for use in improvement of circadian rhythm sleep disorders. Circadian rhythm sleep disorders may be caused by stress, for example, and lead to increased activity during sleep time periods and reduced activity during active time periods. In other words, they result in alterations such as insufficient sleep at nights and drowsiness during the daytime. In most cases when it is attempted to increase the activity level during active time periods using with drugs (the stimulant "methamphetamine", for example), the activity level during sleep time periods also increases. However, the agent for improving circadian rhythm described above increases activity levels during active time periods but does not increase activity levels during sleep time periods, and it is therefore suitable to improve circadian rhythm sleep disorders.

The present invention may also be considered as an agent for use in improving circadian rhythms, comprising a lactic acid bacterium or treated product thereof as the active ingredient. The present invention may further be considered as a method for improving circadian rhythm in a subject in need thereof, comprising administering to the subject an agent comprising a lactic acid bacterium or treated product thereof as the active ingredient. The invention may still further be considered as the use of an agent comprising a lactic acid bacterium or treated product thereof as the active ingredient, for improving circadian rhythm.

The invention further provides a pharmaceutical product, food or beverage, or food or beverage additive containing the aforementioned agent for improving circadian rhythm. The agent for improving circadian rhythm is highly safe for the body and can be continuously ingested for prolonged periods, and it may therefore be used as a pharmaceutical product component, food or beverage component, food or beverage additive, feed component or feed additive.

Advantageous Effects of Invention

According to the invention there is provided a novel agent for improving circadian rhythm that is highly safe for the body and can be used as a component in foods and beverages. The invention further provides a pharmaceutical product, food or beverage, or food or beverage additive containing the agent for improving circadian rhythm.

BRIEF DESCRIPTION OF DRAWINGS

FIG. 6 is a set of graphs showing expression levels of clock genes (Per1, Per2, BMAL1).

DESCRIPTION OF EMBODIMENTS

Figure 1:
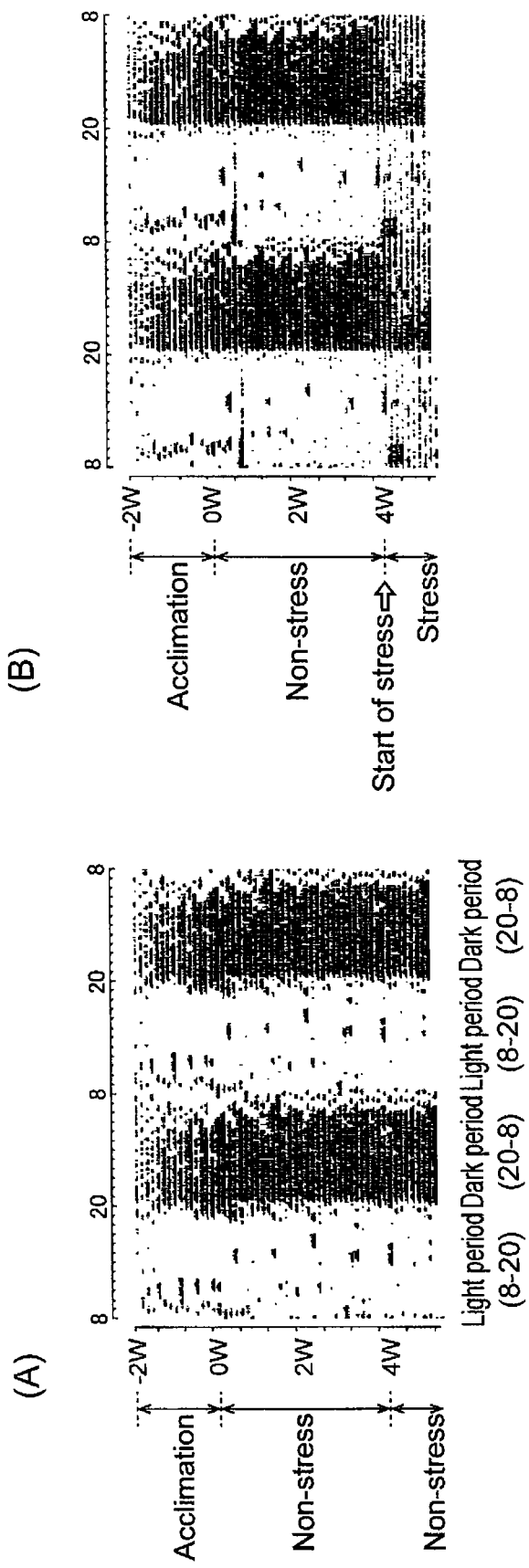
FIG. 1 is a pair of diagrams showing mouse behavioral patterns.

Preferred embodiments of the invention will now be described in detail.

The agent for improving circadian rhythm of the invention comprises cells of lactic acid bacterium or treated product thereof as an active ingredient. From the viewpoint of safety in the body, the lactic acid bacterium is preferably a lactic acid bacterium having a past record of being used in foods such as fermented foods or pharmaceutical products for oral administration. Specific examples include lactic acid bacteria selected from the group consisting of lactic acid bacteria belonging to *Lactobacillus, Bifidobacterium, Enterococcus, Lactococcus, Pediococcus, Leuconostoc* and *Streptococcus.*

The lactic acid bacteria are preferably lactic acid bacteria belonging to *Lactobacillus brevis*, and more preferably they are of *Lactobacillus brevis* SBC8803. The lactic acid bacteria may be ones that are separable from the natural environment, or obtainable from a cell bank such as ATCC.

A single type of lactic acid bacterium, or a combination of two or more different types may be used for the agent for improving circadian rhythm of the invention. The same applies for treated products of the bacterial cells.

The cells of lactic acid bacterium may be live cells or dead cells. The cells can be produced in large quantity by culturing live cells. The medium may be a liquid medium or solid medium, but it preferably contains a nitrogen source and a carbon source. As nitrogen sources there may be used meat extract, peptone, gluten, casein, yeast extract, amino acids and the like, and as carbon sources there may be used glucose, xylose, fructose, inositol, maltose, starch syrup, koji juice, starch, bagasse, bran, molasses, glycerin and the like. As inorganic substances, there may be added ammonium sulfate, potassium phosphate, magnesium chloride, salt, iron, manganese, molybdenum and the like, and vitamins and the like may also be added. Suitable media include MRS medium, LBS medium, Rogosa medium, WYP medium and GYP medium.

The culturing conditions for live cells may employ conditions suitable for the lactic acid bacteria, and for example, the culturing temperature will usually be 20° C. to 50° C., preferably 25° C. to 40° C. and more preferably 30° C. The culturing period will usually be 6 to 62 hours, preferably 12 to 48 hours and more preferably 15 to 30 hours. The medium pH will usually be 3 to 8, preferably 4 to 7 and more preferably 6 to 7. The culturing may be carried out in an incubator, and aerated shaking may be performed during the culturing.

Treated bacterial cells may be a treated product obtained by subjecting the bacterial cells (live cells or dead cells) to treatment such as heating, pressurization, drying, crushing, disruption or autolysis. A combination of two or more different types of such treatment may also be carried out. Examples of treated bacterial cells include treated products obtained by heating bacterial cells for at least several minutes at 100° C. or higher (for example, treated products obtained by autoclave treatment of bacterial cells for 10 minutes or longer at a temperature of 110° C. to 125° C.), treated products obtained by freeze-drying, spray-drying or the like of cells, treated products obtained by contacting bacterial cells with an organic solvent (acetone, ethanol or the like), treated products obtained by contacting bacterial cells with an acid or alkali solution, treated products obtained by enzymatic fragmentation of bacterial cells, or treated products obtained by physical disruption of bacterial cells by ultrasonic waves, French pressing or the like. Such treated bacterial cells are preferred because they are easier to manage than untreated bacterial cells (especially live cells).

The agent for improving circadian rhythm of the invention may be in the form of a solid (for example, powder obtained by freeze-drying), liquid (water-soluble or fat-soluble solution or suspension), paste or the like, and its dosage form may be any kind of form such as a powder, pill, granules, tablet, syrup, troche and capsules.

The formulations mentioned above may consist entirely of the cells of lactic acid bacteria or their treated product as the active ingredient, or they may be prepared, for example, by molding the cells of lactic acid bacterium or their treated product into a dosage form. Each of the aforementioned formulations may be prepared by mixing the active ingredient with a pharmaceutically acceptable additive (an excipient, binder, lubricant, disintegrator, emulsifier, surfactant, base, dissolving aid, suspending agent or the like), and molding the mixture. The active ingredient content in this case is 0.5 to 50 mass % based on the total mass of the formulation.

Examples of excipients include lactose, sucrose, starch and dextrin. Binders include polyvinyl alcohol, gum arabic, tragacanth, gelatin, hydroxypropyl methyl cellulose, hydroxypropyl cellulose, carboxymethyl cellulose sodium and polyvinylpyrrolidone. Lubricants include magnesium stearate, calcium stearate and talc. Disintegrators include crystalline cellulose, agar, gelatin, calcium carbonate, sodium hydrogencarbonate and dextrin. Emulsifiers or surfactants include Tween60, Tween80, Span80 and glycerin monostearate. Bases include cetostearyl alcohol, lanolin, polyethylene glycol, rice bran oil, fish oil (DHA, EPA and the like) and olive oil. Dissolving aids include polyethylene glycol, propylene glycol, sodium carbonate, sodium citrate and Tween80. Suspending agents include Tween60, Tween80, Span 80, glycerin monostearate, polyvinyl alcohol, polyvinylpyrrolidone, methyl cellulose, hydroxymethyl cellulose and sodium alginate.

The agent for improving circadian rhythm of the invention may be administered to a human, or it may be administered to a non-human mammal. The administration dosage and method of administration may be appropriately determined according to the condition, age or the like of the individual to which it is to be administered. Oral administration may be mentioned as an example of a suitable administration method. An example for the dose and method of administration is an amount of the agent for improving circadian rhythm for an active ingredient dose of 0.5 mg to 500 mg, administered orally once a day.

The agent for improving circadian rhythm of the invention can be used as a pharmaceutical product component, food or beverage component, food or beverage additive, feed component, feed additive or the like.

For example, the agent for improving circadian rhythm of the invention may be used as an additive in a food or beverage such as water, a soft drink, fruit drink, milk beverage or alcoholic beverage, bread, noodles, rice, tofu, a dairy product, fermented food, fermented milk, soy sauce, miso, confectionery or the like. These foods and beverages may contain other additives commonly used in the field, and examples of such additives include bittering agents, aromas, apple fiber, soybean fiber, meat extract, black vinegar extract, gelatin, corn starch, honey, animal or vegetable fats and oils, monosaccharides such as glucose and fructose, disaccharides such as sucrose, polysaccharides such as dextrose and starch, sugar alcohols such as erythritol, xylitol, sorbitol and mannitol, and vitamins such as vitamin C. The agent for improving circadian rhythm of the invention may also be used as a component in food for specified health uses, food for special dietary uses, nutritional supplements, health foods, functional foods, patient foods and the like. A food or beverage containing the agent for improving circadian rhythm of the invention may also be a fermentate obtained by fermenting milk, nonfat milk, soybean milk, vegetable, fruit juice, cereal or a processed form thereof with lactic acid bacteria.

The present inventors have found that in mice with stress-induced sleep disorder administered treated bacterial cells of *Lactobacillus brevis* SBC8803, the mRNA expression level of clock genes accelerated by stress-induced sleep disorder is normalized (that is, the level of mRNA expression approaches that of in the absence of stress). Clock genes are known as genes that govern circadian rhythm, and examples include Rev-erb genes (such as Rev-erbα and Rev-erbβ), Clock genes (such as Clock), Per genes (such as Per1 and Per2), Bma1 genes (such as Bma11), Cry genes (such as Cry1 and Cry2) and Dec genes (such as Dec1 and Dec2). Thus, the agent for improving circadian rhythm of the invention improves circadian rhythm based on normalization of mRNA expression levels of clock genes, as at least one of its effects.

Since the agent for improving circadian rhythm of the invention is based on this effect, it can be used for treatment, recovery and amelioration of various alterations, disorders and disease conditions caused by circadian rhythm disturbance or reduction in circadian rhythm function.

That is, the invention may also be considered as an agent for use in treatment, recovery or amelioration of said alterations, disorders or disease conditions, comprising a lactic acid bacterium or treated product thereof as an active ingredient. The invention may further be considered as a treating method, recovering method or ameliorating method for an alteration, disorder or disease condition, comprising administering to a subject an agent comprising a lactic acid bacterium or treated product thereof as the active ingredient. The invention may still further be considered as the use of an agent comprising a lactic acid bacterium or treated product thereof as an active ingredient, for treatment, recovery or amelioration of said alteration, disorder or disease condition.

Examples of such alterations, disorders and disease conditions include circadian rhythm sleep disorders such as stress-induced sleep disorders, autonomic imbalances such as body temperature rhythm disturbances and excessive sympathetic nervous system activity, and bipolar disorder, hypertension, diabetes, bronchial asthma, coronary spastic angina, endocrine dysfunction and the like.

Of these, the agent for improving circadian rhythm of the invention has an effect of improving sleep-wake rhythm, and it is therefore preferably used for treatment, recovery or amelioration of circadian rhythm sleep disorder (that is, it may be a sleep disorder treatment agent, sleep disorder recovery agent or sleep disorder ameliorating agent). A circadian rhythm sleep disorder is a sleep disorder caused by circadian rhythm disturbance or reduction of circadian rhythm function, and for example, it is sleep disorder that is an endogenous acute syndrome resulting from stress-induced sleep disorder, jet lag, shift work or night work, or sleep disorder that is an endogenous chronic syndrome such as delayed sleep phase syndrome, advanced sleep phase syndrome, non-24-hour sleep-wake disorder or irregular sleep-wake pattern.

The agent for improving circadian rhythm of the invention also exhibits an effect of increasing activity levels in dark periods in mice that are in non-stress conditions (that is, mice without occurrence of circadian rhythm sleep disorder). In other words, it can increase the amplitude of the sleep-wake rhythm (that is, increase activity levels during active periods and/or decrease activity level during rest periods). Thus, it can also be used to improve reduction in circadian rhythm function (sleep-wake rhythm, rhythm of hormone secretions such as melatonin, and deep body temperature rhythm) for example due to being older (ageing).

EXAMPLES

The present invention will now be explained in greater detail based on examples. However, the present invention is not limited to the examples described below.

Example 1: Improvement of Circadian Rhythm in Stress-Induced Sleep Disorder Mice Using mice with induced stress-induced sleep disorder, the level of spontaneous behavior of the mice (level of wheel turning behavior, hereunder referred to as "activity level") was used as the index to evaluate the improving effect on circadian rhythm by treated bacterial cells of strain SBL88.

<Preparation of Treated Bacterial Cells>

Strain SBL88 was inoculated into medium (composition: 2 mass % maltose, 1.4 mass % yeast extract, 0.5 mass % sodium acetate, 0.005 mass % manganese sulfate, pH: 6.5 to 7.0), and cultured by stationary culture for 1 day at 30° C. The obtained culture solution (approximately $8\times10^8$ cfu/ml) was centrifuged at 8,000 rpm for 10 minutes, and the bacterial cells were collected. The collected cells were resuspended in distilled water and centrifuged at 8,000 rpm for 10 minutes, and the cells were collected. This procedure was repeated two times. The collected cells were suspended in distilled water and heat treated at 105° C. for 10 minutes, after which it was freeze-dried to obtain a heat treated bacterial cell powder (treated bacterial cells).

<Preparation of Mouse Feed>

After adding 0.5 mass % of the treated cells of strain SBL88 to powdered feed CE-2 (product of Clea Japan, Inc.), the mixture was pelletized to prepare mouse feed containing treated bacterial cells (SBL88-containing CE-2 feed). As a control, powder feed CE-2 was pelletized to prepare mouse feed containing no treated bacterial cells (CE-2 feed).

<Mouse Rearing>

Mice were reared in a rotating cage (SW-15S, product of Melquest, Ltd. for the entire period. The activity level of the mice was measured using a Chronobiology Kit (Stanford Software Systems, Calif.).

C3H/HeN strain mice (3-week-old males, product of Japan SLC, Inc.) were raised for 2 weeks with a light/dark cycle of 12 hours light period, 12 hours dark period (light on at 8:00, light off at 20:00) (acclimation period). Following the acclimation period, the mice were divided into two groups (12 mice per group), and CE-2 feed was given to the control group while SBL88-containing CE-2 feed was given to the test group (SBL88 group), and free access was provided to the feed for 4 weeks (non-stress rearing period).

<Stress Load on Mice>

Following the non-stress rearing period, the mice were physically shielded so that they could not climb down from the rotating wheel, thus inducing stress-induced sleep disorder continuously for 2 weeks (stress rearing period). These stress-induced sleep disorder mice exhibited rhythm disorder that could be generally extrapolated to sleep disorder. Also, total activity levels fell slightly, while disturbance was seen in the behavioral rhythm, with activity during both the light and dark periods. Excessive activity was particularly notable during the first half of the light period. In association with this, there were observed reduced sleep activity during the first half of the light period and increased sleep activity during the active period (dark period).

<Observation of Mouse Behavioral Patterns>

FIG. 1 is a pair of diagrams showing mouse behavioral patterns each day. In FIG. 1, the ordinate represents the rearing period, with the first day of the non-stress rearing period as 0 weeks (0 w) and the first day of the acclimation period as minus 2 weeks (−2 w). The abscissa represents time. The dots represented observed wheel turning behavior of the mice. FIG. 1(A) shows the behavioral pattern for mice without a stress load, and FIG. 1(B) shows the behavioral pattern for mice with a stress load (stress load was initiated after 4 W of the non-stress rearing period). From FIG. 1 it is seen that virtually no wheel turning behavior was observed (few dots) during the light period (8:00-20:00, or the sleep time period). On the other hand, it is seen that active wheel turning behavior was seen during the dark period (20:00-8:00, or the active time period) (numerous dots). Also, it is seen that inducing stress in the mice produced an increase in dots during the light period and a decrease in dots during the dark period, and thus a disturbance in the behavioral pattern.

<Activity Levels of Mice with Stress Load>

Figure 2:
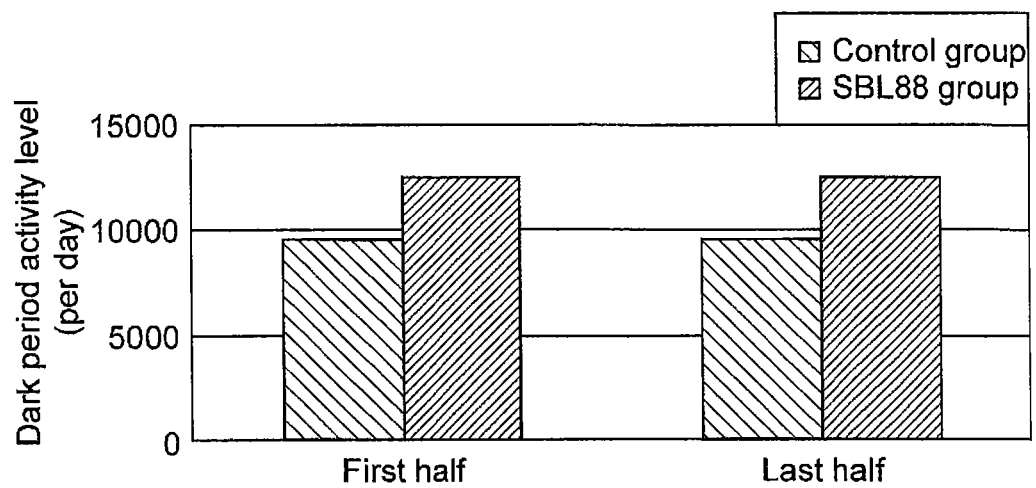
FIG. 2 is a graph showing activity levels per day during dark periods.
Figure 3:
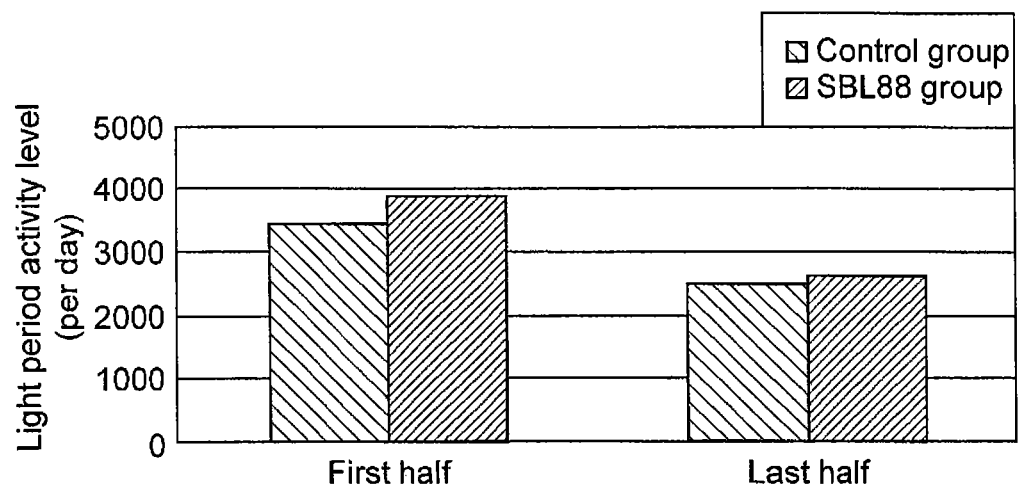
FIG. 3 is a graph showing activity levels per day during light periods.

The activity levels per day of the control group and the SBL88 group were compared for the dark period (20:00-8:00, or the active time period) and the light period (8:00-20:00, or the sleep time period) during the stress rearing period. FIG. 2 is a graph showing activity levels per day during dark periods. FIG. 3 is a graph showing activity levels per day during light periods. In FIG. 2 and FIG. 3, the first week of the stress rearing period (2 week period) was referred as the first half and the remaining week was referred as the last half.

As shown in FIG. 2, the SBL88 group had a statistically significant increase in activity level during the dark period (active time period) compared to the control group (p value (t-test) for each period: first half (0.02), second half (0.05)). On the other hand, no statistically significant difference was found in activity level for the light period (sleep time period) between the SBL88 group and the control group (FIG. 3).

Figure 4:
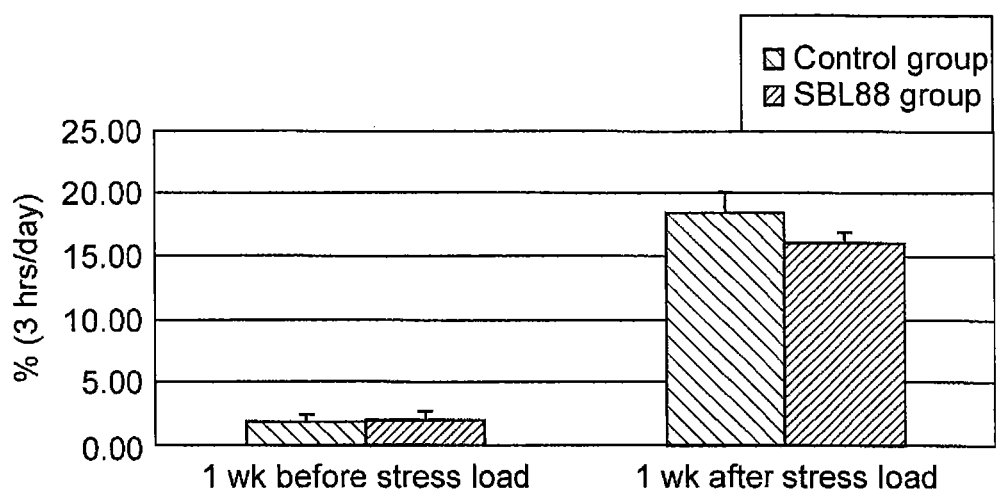
FIG. 4 is a graph showing activity levels during initial light periods, as relative activity levels (%) with respect to total activity levels per day.

FIG. 4 is a graph representing activity level during the initial light period (8:00-11:00) as relative activity level (%) with respect to total activity level per day, for comparison between the SBL88 group and the control group. The characteristic behavioral pattern of the mice seen under stress was reduced activity level during the dark period and excessive activity during the initial light period (8:00-11:00). The graph shown in FIG. 4 is an index of such excessive activity. During the one week period before stress load, no difference in relative activity levels was seen between the SBL88 group and the control group (FIG. 4). On the other hand, 3.0 during the one week period after stress load, the relative activity level was lower in the SBL88 group compared to the control group (FIG. 4). The SBL88 group tended to have less activity acceleration (excessive activity) during the initial light period under stress.

Figure 5:
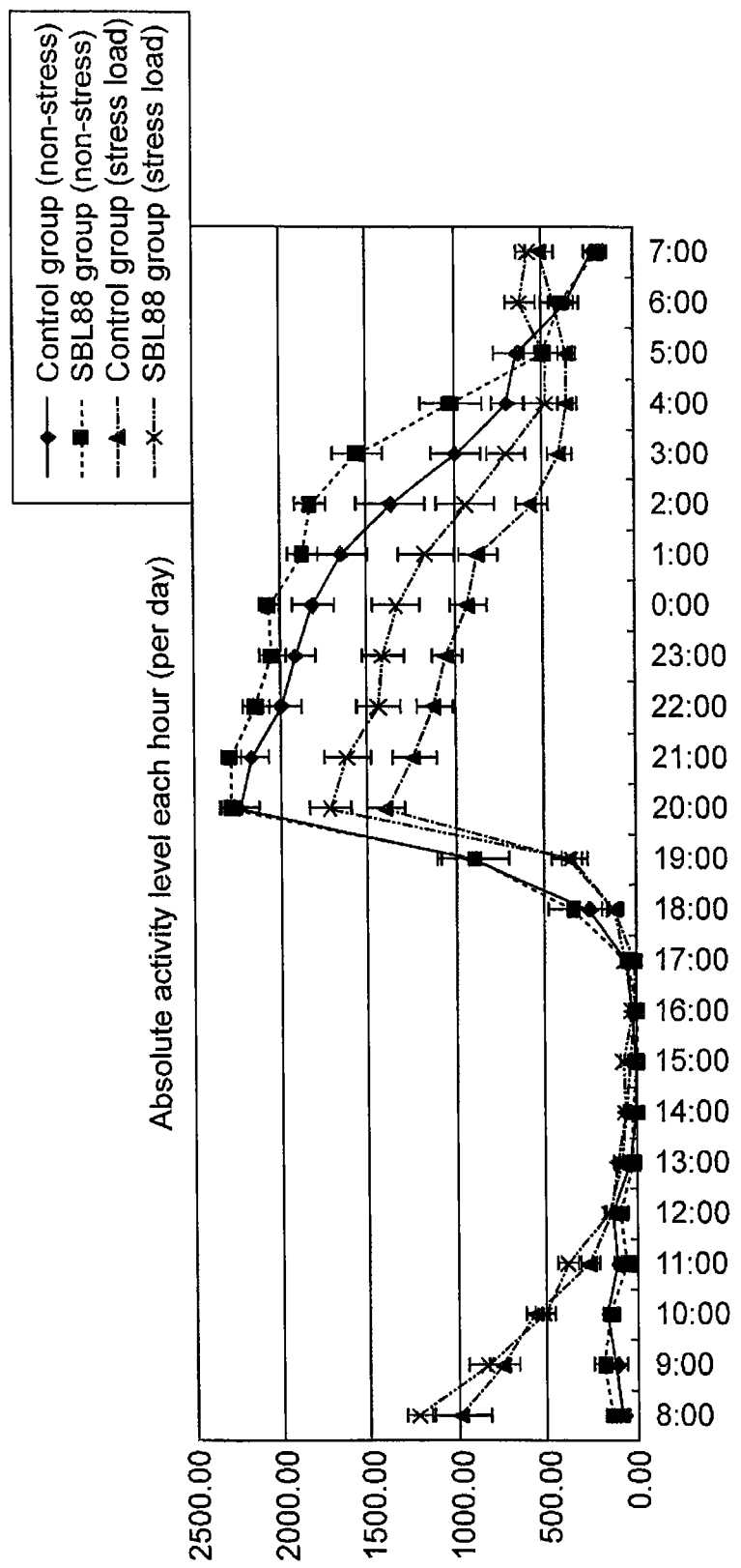
FIG. 5 is a graph showing circadian rhythm of activity levels in mice in the absence of stress and under stress.

FIG. 5 is a graph showing circadian rhythm of activity level for the SBL88 group and control group, during the 7 days before the initial stress load (non-stress) or 6 days after the initial stress load (stress). The ordinate of the graph in FIG. 5 shows the number of rotations of the rotating wheel every hour for the SBL88 group and the control group (mean±standard deviation, n=12). The activity level for each individual was the mean for 7 days before start of the stress load and the mean for 6 days after start of the stress load.

Because mice are nocturnal, spontaneous behavior (wheel turning behavior) is concentrated in the dark period when they are reared in a light-dark cycle. There is also fluctuation in the activity levels during dark periods, with a high activity level during the first half of the dark period and decline of behavior quantity through the middle of the dark period. Whether under stress or in the absence of stress, the SBL88 group significantly increased activity levels through the middle of the dark period, compared to the control group (FIG. 5).

With stress-induced sleep disorder mice, there was observed excessive activity in the first half of the light period, and reduced spontaneous behavior in the dark period which is the original active time period (for example, compare non-stress and stress for the control group in FIG. 5). In the SBL88 group, excessive activity in the first half of the light period due to induced stress-induced sleep disorder was inhibited (FIG. 4), and decrease in activity levels during dark periods was significantly inhibited (FIG. 5).

Mice with stress-induced sleep disorder have reduced activity levels during active time periods, but the reduction in activity levels of mice eating the treated cells of strain SBL88 was significantly inhibited (FIG. 2, FIG. 5). Furthermore, in most cases when it is attempted to increase the activity level during active time periods using with drugs. (the stimulant "methamphetamine", for example), the activity level during sleep time periods also increases. However, mice eating treated cells of SBL88 had activity levels during sleep time periods that were no different from the control group (FIG. 3). That is, the agent for improving circadian rhythm of the invention allows "natural" recovery from sleep disorder.

Example 2: Changes in Expression Levels of Clock Genes

After extracting total mRNA from large intestines of mice that had been killed at 8:00 to 10:00 in the morning on the final day of stress load in Example 1 (after 2 weeks of load), the expression levels of clock genes (Per1, Per2, BMAL1) were examined by quantitative PCR.

FIG. 6 is a set of graphs showing the results of analyzing expression levels of clock genes (Per1, Per2, BMAL1) in large intestine. In FIG. 6, the clock gene expression levels are shown as ratios with respect to β-actin. In the SBL88 group, the expression levels of the Per2 and BMAL1 genes were significantly reduced compared to the control group (FIG. 6). Specifically, expression levels of clock genes (for example, Per2 and BMAL1) that were increased due to sleep disorder stress were modified back to normal expression levels by administration of treated cells of SBL88, and thus circadian rhythm was improved.

The invention claimed is:

1. A method for improving a circadian rhythm sleep disorder in a subject in need thereof, said method comprising administering to the subject an agent comprising at least one strain of a lactic acid bacterium or a treated product thereof, wherein
   the lactic acid bacterium belongs to *Lactobacillus brevis*,
   the subject is not diagnosed with insomnia,
   said agent does not comprise a lactic acid fermentate, and
   said treated product is prepared by subjecting said lactic acid bacterium to at least one treatment selected from the group consisting of heating, pressurization, drying, crushing, disruption, and autolysis.

2. The method according to claim 1, wherein the lactic acid bacterium is *Lactobacillus brevis* SBC8803 (deposit number: FERM BP-10632).

3. The method according to claim 1, wherein improvement of circadian rhythm is based on normalization of a mRNA expression level of a clock gene.

4. The method according to claim 3, wherein the clock gene is Per2 or Bmal1.

5. The method according to claim 1, wherein the circadian rhythm sleep disorder is a stress-induced circadian rhythm sleep disorder.

6. The method according to claim 1, wherein the at least one strain is administered in a pharmaceutical product.

7. The method according to claim 1, wherein the at least one strain is administered in a food or beverage.

8. The method according to claim 1, wherein the at least one strain is administered in a food or beverage additive.

9. The method according to claim 1, wherein said administering to the subject in need thereof comprises administering said agent comprising at least one strain of the lactic acid bacterium.

10. The method according to claim 1, wherein the treated product comprising the at least one strain of lactic acid bacterium is administered to a subject in need thereof.

11. The method according to claim 1, wherein said administering to the subject in need thereof comprises administering said treated product and said treated product is prepared by subjecting said lactic acid bacterium to heating.

12. The method according to claim 1, wherein the agent has from 0.5 to 50 mass % of said at least one strain of a lactic acid bacterium or the treated product thereof.

13. The method according to claim 1, wherein each dose of the agent has from 0.5 to 500 mg of said at least one strain of a lactic acid bacterium or the treated product thereof.

* * * * *